United States Patent
Cao et al.

(10) Patent No.: US 11,130,809 B2
(45) Date of Patent: Sep. 28, 2021

(54) PD-1 ANTIBODY FORMULATION

(71) Applicant: INNOVENT BIOLOGICS (SUZHOU) CO., LTD., Jiangsu (CN)

(72) Inventors: Wei Cao, Jiangsu (CN); Junfeng Li, Jiangsu (CN); Xiaolin Liu, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 420 days.

(21) Appl. No.: 16/322,630

(22) PCT Filed: Jul. 17, 2017

(86) PCT No.: PCT/CN2017/093141
§ 371 (c)(1),
(2) Date: Feb. 1, 2019

(87) PCT Pub. No.: WO2018/028383
PCT Pub. Date: Feb. 15, 2018

(65) Prior Publication Data
US 2021/0040211 A1    Feb. 11, 2021

(30) Foreign Application Priority Data
Aug. 9, 2016    (WO) ................ PCT/CN2016/094094

(51) Int. Cl.
*C07K 16/28* (2006.01)
*A61K 47/26* (2006.01)

(52) U.S. Cl.
CPC .......... *C07K 16/2818* (2013.01); *A61K 47/26* (2013.01)

(58) Field of Classification Search
None
See application file for complete search history.

(56) References Cited

U.S. PATENT DOCUMENTS

2010/0172862 A1* 7/2010 Correia ................... A61P 37/02
424/85.2

FOREIGN PATENT DOCUMENTS

| JP | 2013521768 A | 6/2013 |
|---|---|---|
| JP | 2014515017 A | 6/2014 |
| JP | 2016155827 A | 9/2016 |
| WO | 2004056875 | 7/2004 |
| WO | 2006121168 | 11/2006 |
| WO | 2011110604 | 9/2011 |
| WO | 2011110621 | 9/2011 |
| WO | 2012135408 | 10/2012 |
| WO | 2016011357 | 1/2016 |
| WO | 2016032927 | 3/2016 |
| WO | 2016092419 | 6/2016 |
| WO | 2017024465 A1 | 2/2017 |
| WO | 2017025016 A1 | 2/2017 |

OTHER PUBLICATIONS

Daughtery, A.L. et al. "Formulation and delivery issues for monoclonal antibody therapeutics." Advanced Drug Delivery Reviews., vol. 58, May 22, 2006, p. 686-706.
International Search Report and Written Opinion dated Sep. 28, 2017 corresponding to International Patent Application No. PCT/CN2017/093141, 14 pages.
Office Action in Japanese Application JP2019-507084 dated Jun. 2, 2020.
Extended European Search Report in EP application No. EP17838513.4, dated Feb. 28, 2020.
Wang W et al: "Antibody Structure, Instability, and Formulation", Journal of Pharmaceutical Sciences, American Pharmaceutical Association, US, vo 1 • 96, No. 1, 2007, pp. 1-26.
Examination report No. 1 in Australian application 2017310916, dated Oct. 23, 2019.
Office Action in Brazilian application BR112019001233-8, dated Jun. 30, 2020.
Office Action in Canadian application 3,030,929, dated Nov. 19, 2019.

* cited by examiner

*Primary Examiner* — Nelson B Moseley, II
(74) *Attorney, Agent, or Firm* — Leason Ellis LLP

(57) ABSTRACT

Provided herein are pharmaceutical formulations for anti-PD-1 antibodies.

14 Claims, No Drawings
Specification includes a Sequence Listing.

SEQUENCE LISTING

```
<160> NUMBER OF SEQ ID NOS: 4

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
```

```
            115                 120                 125
Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Ser Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                195                 200                 205
Phe Asn Arg Gly Glu Cys
    210

<210> SEQ ID NO 3
<211> LENGTH: 447
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
```

```
              340                 345                 350
Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 4
<211> LENGTH: 446
<212> TYPE: PRT
<213> ORGANISM: Artificial Sequence
<220> FEATURE:
<223> OTHER INFORMATION: Synthetic Construct

<400> SEQUENCE: 4

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Ser Thr Ala Tyr
65              70                  75                  80

Met Glu Leu Ser Ser Leu Arg Ser Glu Asp Thr Ala Val Tyr Tyr Cys
            85                  90                  95

Ala Arg Ala Glu His Ser Ser Thr Gly Thr Phe Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
```

```
                260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly
                435                 440                 445
```

PD-1 ANTIBODY FORMULATION

The present invention relates to the field of medicine. More particularly, the present invention relates to a pharmaceutical formulation of an anti-human programmed cell death 1 (anti-PD-1) antibody. This anti-PD-1 antibody pharmaceutical formulation is expected to be useful in treating cancers that respond to anti-PD-1 antibodies as a monotherapy and in combination with chemotherapy and other cancer therapeutics.

Pharmaceutical formulations of anti-PD-1 antibodies are needed for the treatment of patients with cancer. Certain concentrations of anti-PD-1 antibodies are needed for pharmaceutical formulations so that the antibody can be delivered intra-venously to the patient. This pharmaceutical formulation with a certain concentration of the anti-PD-1 antibody must maintain physical and chemical stability of the anti-PD-1 antibody over long periods of time in storage. For use of the anti-PD-1 antibody worldwide under conditions that can vary significantly, the formulation should not only maintain stability of the anti-PD-1 antibody for periods of time at room temperature, but maintain stability under possible fluctuations in temperature and under potential exposures to light.

Anti-PD-1 antibodies used in the present pharmaceutical formulations are disclosed in PCT/CN2015/086494. Those antibodies were discovered to be prone to chemical instability, including oxidation, when stored over a long period of time and under various environmental conditions. Thus, pharmaceutical formulations for anti-PD-1 antibodies are needed that avoid these observed problems and also demonstrate stability during extended shelf life.

Accordingly, the present invention provides a pharmaceutical formulation comprising an anti-PD-1 antibody at a concentration in the range of about 5 mg/mL to about 15 mg/mL, citrate at a concentration of about 15 mM to about 25 mM, histidine at a concentration of about 20 mM to about 30 mM, mannitol at a concentration of about 130 mM to about 165 mM, sodium chloride at a concentration of about 45 mM to about 55 mM, edetate at a concentration of about 0.01 mM to about 0.03 mM, polysorbate 20 or polysorbate 80 at a concentration in the range of about 0.01% to about 0.03%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration of about 10 mg/mL, citrate at a concentration of about 15 mM to about 25 mM, histidine at a concentration of about 20 mM to about 30 mM, mannitol at a concentration of about 130 mM to about 165 mM, sodium chloride at a concentration of about 45 mM to about 55 mM, edetate at a concentration of about 0.01 mM to about 0.03 mM, polysorbate 20 or polysorbate 80 at a concentration in the range of about 0.01% to about 0.03%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration in the range of about 5 mg/mL to about 15 mg/mL, citrate at a concentration of about 20 mM, histidine at a concentration of about 20 mM to about 30 mM, mannitol at a concentration of about 130 mM to about 165 mM, sodium chloride at a concentration of about 45 mM to about 55 mM, edetate at a concentration of about 0.01 mM to about 0.03 mM, polysorbate 20 or polysorbate 80 at a concentration in the range of about 0.01% to about 0.03%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration in the range of about 5 mg/mL to about 15 mg/mL, citrate at a concentration of about 15 mM to about 25 mM, histidine at a concentration of about 25 mM, mannitol at a concentration of about 130 mM to about 165 mM, sodium chloride at a concentration of about 45 mM to about 55 mM, edetate at a concentration of about 0.01 mM to about 0.03 mM, polysorbate 20 or polysorbate 80 at a concentration in the range of about 0.01% to about 0.03%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration in the range of about 5 mg/mL to about 15 mg/mL, citrate at a concentration of about 15 mM to about 25 mM, histidine at a concentration of about 20 mM to about 30 mM, mannitol at a concentration of about 140 mM, sodium chloride at a concentration of about 45 mM to about 55 mM, edetate at a concentration of about 0.01 mM to about 0.03 mM, polysorbate 20 or polysorbate 80 at a concentration in the range of about 0.01% to about 0.03%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration in the range of about 5 mg/mL to about 15 mg/mL, citrate at a concentration of about 15 mM to about 25 mM, histidine at a concentration of about 20 mM to about 30 mM, mannitol at a concentration of about 130 mM to about 165 mM, sodium chloride at a concentration of about 50 mM, edetate at a concentration of about 0.01 mM to about 0.03 mM, polysorbate 20 or polysorbate 80 at a concentration in the range of about 0.01% to about 0.03%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention provides a pharmaceutical formulation comprising an anti-PD-1 antibody at a concentration in the range of about 5 mg/mL to about 15 mg/mL, citrate at a concentration of about 15 mM to about 25 mM, histidine at a concentration of about 20 mM to about 30 mM, mannitol at a concentration of about 130 mM to about 165 mM, sodium chloride at a concentration of about 45 mM to about 55 mM, edetate at a concentration of about 0.02 mM, polysorbate 20 or polysorbate 80 at a concentration in the range of about 0.01% to about 0.03%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration in the range of about 5 mg/mL to about 15 mg/mL, citrate at a concentration of about 15 mM to about 25 mM, histidine at a concentration of about 20 mM to about 30 mM, mannitol at a concentration of about 130 mM to about 165 mM, sodium chloride at a concentration of about 45 mM to about 55 mM, edetate at a concentration of about 0.01 mM to about 0.03 mM, polysorbate 20 or polysorbate 80 at a concentration of about 0.02%, and pH of about 5.5 to about 6.5, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration in the range of about 5 mg/mL to about 15 mg/mL, citrate at a concentration of about 15 mM to about 25 mM, histidine at a concentration of about 20 mM to about 30 mM, mannitol at a concentration of about 130 mM to about 165 mM, sodium chloride at a concentration of about 45 mM to about 55 mM, edetate at a concentration of about 0.01 mM to about 0.03 mM, polysorbate 20 or polysorbate 80 at a concentration in the range of about 0.01% to about 0.03%, and pH of about 6.0, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration of about 10 mg/mL, citrate at a concentration of about 20 mM, histidine at a concentration of about 25 mM, mannitol at a concentration of about 140 mM, sodium chloride at a concentration of about 50 mM, edetate at a concentration of about 0.02 mM, polysorbate-80 at a concentration of about 0.02%, and pH at about 6.0, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

The present invention also provides a pharmaceutical formulation comprising an anti-PD-1 antibody at a concentration of about 10 mg/mL, citrate at a concentration of about 20 mM, histidine at a concentration of about 25 mM, mannitol at a concentration of about 140 mM, sodium chloride at a concentration of about 50 mM, edetate at a concentration of about 0.02 mM, polysorbate-20 at a concentration of about 0.02%, and pH at about 6.0, wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

In an embodiment, the present invention also provides a pharmaceutical formulation that comprises a concentration of anti-PD-1 antibody of about 5 mg/mL to about 15 mg/mL. In another embodiment, the present invention provides a pharmaceutical formulation that comprises a concentration of anti-PD-1 antibody of about 5 mg/mL. In another embodiment, the present invention provides a pharmaceutical formulation that comprises a concentration of anti-PD-1 antibody of about 10 mg/mL. In another embodiment, the present invention provides a pharmaceutical formulation that comprises a concentration of anti-PD-1 antibody of about 15 mg/mL.

In an embodiment, the present invention also provides a pharmaceutical formulation that is buffered with citrate in the range of about 15 mM to about 25 mM. In another embodiment, the present invention provides a pharmaceutical formulation that is buffered with citrate in the range of 15 mM to 25 mM. In another embodiment, the present invention provides a pharmaceutical formulation that is buffered with citrate at a concentration of about 15 mM, about 20 mM, or about 25 mM. In a further embodiment, the present invention provides a pharmaceutical formulation that is buffered with citrate at a concentration of about 20 mM.

In another embodiment, the present invention provides a pharmaceutical formulation that is buffered with histidine in the range of 20 mM to 30 mM. In another embodiment, the present invention provides a pharmaceutical formulation that is buffered with histidine at a concentration of about 20 mM, about 25 mM, or about 30 mM. In a further embodiment, the present invention provides a pharmaceutical formulation that is buffered with histidine at a concentration of about 25 mM.

In an embodiment, the present invention also provides a pharmaceutical formulation that comprises a concentration of mannitol of about 130 mM to about 165 mM. In another embodiment, the present invention provides a pharmaceutical formulation that comprises a concentration of mannitol of about 130 mM, about 135 mM, about 140 mM, about 145 mM, about 150 mM, about 155 mM, about 160 mM, or about 165 mM. In a further embodiment, the present invention provides a pharmaceutical formulation that comprises a concentration of mannitol of about 140 mM.

In an embodiment, the present invention also provides a pharmaceutical formulation that comprises a concentration of NaCl of about 45 mM to about 55 mM. In another embodiment, the present invention provides a pharmaceutical formulation that comprises a concentration of NaCl of about 45 mM, about 50 mM, or about 55 mM. In a further embodiment, the present invention provides a pharmaceutical formulation that comprises a concentration of NaCl of about 50 mM.

In an embodiment, the present invention also provides a pharmaceutical formulation that comprises a concentration of edetate of about 0.01 mM to about 0.03 mM. In another embodiment, the present invention provides a pharmaceutical formulation that comprises a concentration of disodium edetate of about 0.01 mM, about 0.015 mM, about 0.02 mM, about 0.025 mM, or about 0.03 mM. In a further embodiment, the present invention provides a pharmaceutical formulation that comprises a concentration of disodium edetate of about 0.02 mM.

In an embodiment, the present invention also provides a pharmaceutical formulation that comprises a concentration of polysorbate-80 or polysorbate-20 of about 0.01% to about 0.03%. In another embodiment, the present invention provides a pharmaceutical formulation that comprises a concentration of polysorbate-80 of about 0.01%, about 0.015%, about 0.02%, about 0.025%, or about 0.03%. In a further embodiment, the present invention provides a pharmaceutical formulation that comprises a concentration of polysorbate-80 of about 0.02%.

In an embodiment, the present invention also provides a pharmaceutical formulation within a pH range of about 5.5 to about 6.5. In another embodiment, the present invention provides a pharmaceutical formulation that comprises a pH of about 5.5, about 6.0, or about 6.5. In a further embodiment, the present invention provides a pharmaceutical formulation that comprises a pH of about 6.0.

Certain pharmaceutical formulations are preferred. The following enumerated selections describe such preferred classes:
1) the anti-PD-1 antibody comprises an antibody comprising two light chains (LCs) and two heavy chains (HCs), wherein each LC is the amino acid sequence of SEQ ID NO: 2 and each HC is the amino acid sequence of SEQ ID NO: 3 or the amino acid sequence of SEQ ID NO: 4;
2) the anti-PD-1 antibody at a concentration of about 5 mg/mL to about 15 mg/mL;
3) the anti-PD-1 antibody at a concentration of about 10 mg/mL;
4) polysorbate-80 is at a concentration of about 0.01% to about 0.03%
5) polysorbate-80 is at a concentration of about 0.02%
6) polysorbate-20 is at a concentration of about 0.01% to about 0.03%;
7) polysorbate-20 is at a concentration of about 0.02%
8) citrate is at a concentration of about 15 mM to about 25 mM;
9) citrate is at a concentration of about 20 mM;
10) histidine is at a concentration of about 20 mM to about 30 mM;
11) histidine is at a concentration of about 25 mM;
12) mannitol is at a concentration of about 130 mM to about 165 mM;
13) mannitol is at a concentration of about 140 mM;
14) sodium chloride is at a concentration of about 45 mM to about 55 mM;
15) sodium chloride is at a concentration of about 50 mM;
16) edetate is at a concentration in the range of about 0.01 to about 0.03 mM.
17) edetate is at a concentration of about 0.02 mM;
18) histidine is at a concentration of about 25 mM and citrate at a concentration of about 20 mM.
19) the pH is 5.5 to 6.5.
20) the pH is about 6.0.

In addition, the present invention provides a method of treating cancers that may respond to anti-PD-1 antibodies comprising administering to a patient in need thereof an effective amount of a pharmaceutical formulation described herein. Furthermore, the method of treating cancer comprising administering to a patient in need thereof an effective amount of a pharmaceutical formulation of the present invention, wherein the cancer is selected from the group of melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma. More particularly, the present invention provides a method of treating melanoma comprising administering to a patient in need thereof an effective amount of a pharmaceutical formulation of the present invention. Also, the present invention provides a method of treating lung cancer comprising administering to a patient in need thereof an effective amount of a pharmaceutical formulation of the present invention. Also, the present invention provides a method of treating head and neck cancer comprising administering to a patient in need thereof an effective amount of a pharmaceutical formulation of the present invention. Also, the present invention provides a method of treating colorectal cancer comprising administering to a patient in need thereof an effective amount of a pharmaceutical formulation of the present invention. Also, the present invention provides a method of treating pancreatic cancer comprising administering to a patient in need thereof an effective amount of a pharmaceutical formulation of the present invention. Also, the present invention provides a method of treating gastric cancer comprising administering to a patient in need thereof an effective amount of a pharmaceutical formulation of the present invention. Also, the present invention provides a method of treating kidney cancer comprising administering to a patient in need thereof an effective amount of a pharmaceutical formulation of the present invention. Also, the present invention provides a method of treating bladder cancer comprising administering to a patient in need thereof an effective amount of a pharmaceutical formulation of the present invention. Also, the present invention provides a method of treating prostate cancer comprising administering to a patient in need thereof an effective amount of a pharmaceutical formulation of the present invention. Also, the present invention provides a method of treating breast cancer comprising administering to a patient in need thereof an effective amount of a pharmaceutical formulation of the present invention. Also, the present invention provides a method of treating ovarian cancer comprising administering to a patient in need thereof an effective amount of a pharmaceutical formulation of the present invention. Also, the present invention provides a method of treating hepatocellular carcinoma comprising administering to a patient in need thereof an effective amount of a pharmaceutical formulation of the present invention. In addition, the present invention provides the pharmaceutical formulation of the present invention for use in treating cancer. In addition, the present invention provides the pharmaceutical formulation of the present invention for use in the treatment of melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma. More particularly, the present invention provides the pharmaceutical formulation of the present invention for use in the treatment of melanoma. Also, the present invention provides the pharmaceutical formulation of the present invention for use in the treatment of lung cancer. Also, the present invention provides the pharmaceutical formulation of the present invention for use in the treatment of head and neck cancer. Also, the present invention provides the pharmaceutical formulation of the present invention for use in the treatment of colorectal cancer. Also, the present invention provides the pharmaceutical formulation of the present invention for use in the treatment of gastric cancer. Also, the present invention provides the pharmaceutical formulation of the present invention for use in the treatment of colorectal cancer. Also, the present invention provides the pharmaceutical formulation of the present invention for use in the treatment of kidney cancer. Also, the present invention provides the pharmaceutical formulation of the present invention for use in the treatment of bladder cancer. Also, the present invention provides the pharmaceutical formulation of the present invention for use in the treatment of prostate cancer. Also, the present invention provides the pharmaceutical formulation of the present invention for use in the treatment of breast cancer. Also, the present invention provides the pharmaceutical formulation of the present invention for use in the treatment of ovarian cancer. Also, the present invention provides the pharmaceutical formulation of the present invention for use in the treatment of hepatocellular carcinoma.

The pharmaceutical formulations of the present invention comprise citrate. Citrate can be made using one or more of citric acid, trisodium citrate dihydrate, and citric acid monohydrate; or citric acid monohydrate, sodium phosphate dibasic, and citric acid. Also, citrate can be made comprising sodium citrate monobasic, citric acid trisodium salt, or sodium citrate tribasic hydrate. Preferably, citrate is made with sodium citrate dihydrate and citric acid. Other counterions besides sodium may be used.

The pharmaceutical formulations of the present invention comprise edetate. Preferably edetate is edetate disodium (EDTA.2Na).

Antibody 1 is an anti-PD-1 antibody comprising two light chains (LCs) and two heavy chains (HCs), wherein the amino acid sequence of each LC is SEQ ID NO: 2 and the amino acid sequence of each HC is SEQ ID NO: 3.

Antibody 2 is an anti-PD-1 antibody comprising two light chains (LCs) and two heavy chains (HCs), wherein the amino acid sequence of each LC is SEQ ID NO: 2 and the amino acid sequence of each HC is SEQ ID NO: 4.

An anti-PD-1 antibody for use in the formulations of the present invention can be produced using techniques well known in the art, e.g., recombinant technologies, phage display technologies, synthetic technologies, or combinations of such technologies or other technologies readily known in the art. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

Antibodies 1 and 2 can be prepared in mammalian expression systems that are commonly used for industrial-scale cell culture using ordinary skill in the antibody art. As expressed in such common mammalian expression systems, such as CHO or NSO, the expressed antibodies will have the expected disulfide bonds within and between the chains. Furthermore, the antibodies will be glycosylated within CH2.

To be considered stable, an antibody in solution must have sufficient chemical stability and physical stability. Oxidation, deamidation, and hydrolysis are examples of chemical stability issues that an antibody can have in a formulation. Aggregation and gel formation are examples of physical stability issues that an antibody can have in a formulation. A pharmaceutical formulation of an antibody is considered stable if the degree of degradation, modification, aggregation, loss of biological activity and the like, of the antibody therein is acceptably controlled and does not increase unacceptably with time. Stability may be assessed by methods well-known in the art, including measurement of a sample's light scattering, apparent attenuation of light (absorbance, or optical density), size of aggregates or other polymerized forms of the antibody (e.g. by size exclusion chromatography (SEC)), in vitro or in vivo biological activity and/or properties measured by differential scanning calorimetry (DSC). Other methods for assessing stability are well known in the art and can also be used according to the present invention.

As mentioned, the present invention provides a method of treating cancers that may respond to anti-PD-1 antibodies comprising administering to a patient in need thereof an effective amount of a pharmaceutical formulation described herein. An effective amount of the anti-PD-1 antibody formulation of the present invention is the quantity that when administered to a patient in need of treatment results in the desired therapeutic effect without causing unacceptable side-effects when administered to a subject with increased PD-1 levels.

EXAMPLE 1

Solid buffer ingredients are weighed and transferred to a beaker to which 80% of the target volume of dd $H_2O$ is added and the mixture is stirred with a magnetic stirrer to dissolve the ingredients. After all ingredients are dissolved, the pH of the solution is adjusted to 6.0 using 2 M citric acid and dd $H_2O$ is added to achieve the target volume. Polysorbate 80 is then prepared at 20 mg/mL using the initial buffer to attain a 100×concentration of polysorbate 80. Antibody samples are concentrated to about 15 mg/mL using an Amicon Ultra-30K centrifugal filter at 3800 g. Concentrated antibody samples are subjected to 6-7 rounds of buffer-exchange in the initial buffer. Buffer exchanged antibody samples are diluted with the initial buffer and 100x polysorbate 80 to achieve a final concentration of 10 mg/mL of antibody and 0.2 mg/mL of polysorbate 80. Samples are sterile filtered with 0.22 μm filter to obtain the final drug product.

TABLE 1

Antibody Drug Product Formulation

| Component | Concentration |
| --- | --- |
| Antibody | 10 mg/mL |
| Sodium Citrate | 20 mM |
| Histidine | 25 mM |
| Mannitol | 140 mM |
| Sodium Chloride | 50 mM |
| Edetate (EDTA.2Na) | 0.02 mM |
| Polysorbate 80 | 0.02% |
| pH | 6.0 |

TABLE 2

Antibody Drug Product Formulation

| Component | Concentration |
| --- | --- |
| mAb | 5-15 mg/mL |
| Sodium Citrate | 15-25 mM |
| Histidine | 20-30 mM |
| Mannitol | 130-165 mM |
| Sodium Chloride | 45-55 mM |
| Edetate (EDTA.2Na) | 0.01-0.03 mM |
| Polysorbate 80 or Polysorbate 20 | 0.1-0.3% |
| pH | 5.5-6.5 |

Effect of pH

For a pharmaceutical formulation to achieve stability, both physical and chemical sources of instability need to be addressed in the formulation. Chemical instability can result in degradation of the antibody.

In order to assess the effect of pH on the chemical stability of Antibody 1 at 5 mg/mL, samples of Antibody 1 are analyzed in citrate buffer at varying pH. The citrate buffer is prepared at 10 mM in double-distilled water (dd $H_2O$) and the pH of the buffer is adjusted to a pH of 4, 5, 6, 7 or 8. Antibody 1 is diluted at 5 mg/mL in the various pH adjusted citrate buffers and is incubated at 37° C. for 10 days. The samples are tested at Day 0 and Day 10 via SEC-HPLC (Size Exclusion Chromatography-High Performance Liquid Chromatography) as per the Pharmacopoeia of the People's Republic of China, (Edition 2010, Section 3, Appendix IIIB), and are detected via hydrophilic silica gel size exclusion columns, and sample purity is measured by area normalization. The Day 0 main peak area % was 98.65%.

The results as demonstrated in Table 3, indicate that Antibody 1 is most stable at a pH of 6, and only slightly less stable at a pH of 5. Antibody 1 is least stable at more acidic pH conditions or more alkaline pH conditions. These results indicate that the pH of the pharmaceutical solution formulation for Antibody 1 should be between pH 5 and pH 6.

TABLE 3

SEC-HPLC results of the effect of pH on Antibody 1 at 5 mg/mL in Citrate Buffer

| pH | Main peak area % Day 10 @ 37° C. | Change from Day 0 |
|---|---|---|
| 4.0 | 5.95 | −92.7 |
| 5.0 | 97.77 | −0.88 |
| 6.0 | 98.36 | −0.29 |
| 7.0 | 96.38 | −2.27 |
| 8.0 | 96.57 | −2.08 |

Effects of Buffer, Polyhydric Alcohols, Surfactant and other Excipients on the Stability of Antibody 1

The effects of commonly used buffers on the stability of Antibody are explored to understand what the optimal buffer system would be for Antibody 1. The study uses a multivariate approach to examine the physical and chemical stability of Antibody 1 solution formulations. Antibody 1 solution formulations are prepared according to Table 4. Phosphate buffer and Citrate buffer are prepared in dd $H_2O$ at 20 mM. Various test excipients as shown in Table 4 are tested to determine the optimal formulation for Antibody 1. Excipients are added to the various buffers and the pH is adjusted to 6.0 for each sample. Test samples are incubated at 25° C. for up to three months. Samples are tested for stability at Day 0, and at Months 1 and 3 via CEX-HPLC (Ion Exchange Chromatography-High Performance Liquid Chromatography) as per the Pharmacopoeia of the People's Republic of China, (Edition 2010, Section three, Appendix IIIB), and is detected with cation columns, and sample purity is measured by area normalization. The results are illustrated in Table 5.

TABLE 4

Design for Formulation Testing for Antibody 1

| Sample | Citrate | Phosphate | Mannitol | Sucrose | Methionine | Histidine | Pentenic Acid | Edetate Disodium |
|---|---|---|---|---|---|---|---|---|
| F1 | 20 | | 165 | | | | 0.02 | |
| F2 | | 20 | 165 | | | | | 0.02 |
| F3 | 20 | | 165 | | | | | 0.02 |
| F4 | 20 | | | 165 | | | | 0.02 |
| F5 | 20 | | 140 | | 25 | | | 0.02 |
| F6 | 20 | | 140 | | | 25 | | 0.02 |

Values are mM.

Each tested formulation comprised 10 mg/mL of Antibody 1, 50 mM sodium chloride, and 0.02% polysorbate, and each had its pH adjusted to 6.0.

TABLE 5

CEX-HPLC results of buffer effects on Antibody 1

| | 0 Day | | | 1 Month | | | 3 Months | | |
|---|---|---|---|---|---|---|---|---|---|
| | Acidic | Main | Basic | Acidic | Main | Basic | Acidic | Main | Basic |
| F1 | 19.6 | 73.7 | 6.8 | 22.5 | 72.9 | 4.6 | 28.8 | 67.8 | 3.4 |
| F2 | 19.7 | 73.7 | 6.6 | 23.6 | 73.2 | 3.2 | 27.5 | 69.3 | 3.2 |
| F3 | 19.6 | 73.8 | 6.6 | 22.5 | 72.7 | 4.8 | 28.9 | 67.8 | 3.4 |
| F4 | 19.7 | 73.5 | 6.8 | 22.5 | 72.7 | 4.9 | 29.2 | 67.6 | 3.2 |
| F5 | 19.8 | 73.5 | 6.7 | 22.5 | 72.8 | 4.6 | 28.9 | 67.9 | 3.2 |
| F6 | 19.4 | 73.8 | 6.7 | 22.4 | 73.5 | 4.1 | 28.1 | 69.1 | 2.9 |

Values are % of CEX-HPLC eluate.

The results demonstrate that formulation test samples F2 and F6 have a slower increase in acidic species, which not only indicates that the formulation of F2 and F6 provided a more stable environment for Antibody 1 when compared to the other formulations tested, but surprisingly showed that the unique combination of polysorbate 80, mannitol and histidine in citrate buffer provide enhanced stability for Antibody 1.

Effects of Light Exposure on the Stability of Antibody 1

The formulation and conditions of test samples F2 and F6 are duplicated to test for light sensitivity testing of Antibody 1. Test samples F2 and F6 containing Antibody 1 at 10 mg/mL are exposed to a high intensity fluorescent light (5000 Lux) at 25° C. for 10 days. The samples are tested for stability at Day 0, Day 5 and Day 10 using CEX-HPLC and SEC-HPLC technology.

TABLE 6

CEX-HPLC and SEC-HPLC Results of Light Exposure on Antibody 1

| | 25° C., 5000Lux | 0 day | 5 days | 10 days |
|---|---|---|---|---|
| F 2 | Acidic component | 12.6 | 17.9 | 21.6 |
| | Main component | 77.6 | 73.4 | 70.0 |
| | Basic component | 9.8 | 8.7 | 8.4 |
| | Main peak content | 97.3 | 95.6 | 94.6 |
| F 6 | Acidic component | 12.4 | 15.2 | 19.0 |
| | Main component | 77.7 | 75.7 | 72.3 |
| | Basic component | 9.9 | 9.2 | 8.7 |
| | Main peak content | 97.5 | 97.3 | 96.8 |

Values are %.

The results shown in Table 6 surprisingly demonstrate that the formulation of test sample F6 provides greater anti-oxidative properties for Antibody 1 when compared to formulation test sample F2 and consequently resulting in enhanced stability and anti-oxidation properties for Antibody 1.

Accelerated Stability Testing of Antibody 1

Antibody 1 is tested for stability via an accelerated stability testing method, using the formulation F6. Antibody 1 in the above formulation is aseptically dispensed in to glass vials, and is sealed with rubber stoppers and plastic covers and is incubated at 25° C.±2° C. for 1 month. The samples are tested for stability at Day 0 and at 1 Month using CEX-HPLC and SEC-HPLC technology.

The accelerated stability test results are illustrated in Table 7 and Table 8. The results demonstrate that the purity and the overall stability of Antibody 1 in the aforementioned formulation were not significantly affected after a 1 month incubation period under the accelerated conditions. Further analysis on appearance, concentration, turbidity also showed similar results. The formulation was thus shown to be able to maintain the stability of Antibody 1 for at least one month at 25° C.

TABLE 7

CEX-HPLC and SEC-HPLC Results of Accelerated Stability Testing of Antibody 1 at 25° C. ± 2° C.

| | Day 0 | 1 month |
|---|---|---|
| Acidic component | 19.4 | 22.4 |
| Main component | 73.8 | 73.5 |
| Basic component | 6.7 | 4.1 |
| Main peak area | 99.4 | 99.2 |

Values are %.

Long-Term Stability Testing of Antibody 1

Biologic drug products are stored at 5° C.±3° C. to minimize chemical and physical degradation over the shelf-life of a product. Antibody 1 at 10 mg/mL is tested for long-term stability in the formulation F6.

Antibody 1 is aseptically dispensed in to vials, and is sealed with rubber stoppers and plastic covers and is incubated at 2° C. to about 8° C. for 11 months. The samples are tested for stability at Day 0 and at 3, 6 and 11 month time points using CEX-HPLC and SEC-HPLC technology The long term stability test results are illustrated in Table 9 and Table 10. The results demonstrate that the purity and the overall stability of Antibody 1 in the aforementioned formulation was not significantly affected after an 11 month incubation period under the long term conditions. Further analysis on appearance, concentration, turbidity also showed similar results. This unique formulation in addition to the previously exemplified stability benefits, was further shown to be able to maintain the stability of Antibody 1 for at least 11 months at 2° C. to about 8° C.

TABLE 8

CEX-HPLC and SEC-HPLC Results of Long-Term Stability Testing at 2 to 8° C. of Antibody 1

| | 0 day | 3 months | 6 months | 11 months |
|---|---|---|---|---|
| Acidic component | 15.4 | 15.7 | 15.9 | 15.2 |
| Main component | 80.6 | 80.5 | 79.1 | 80.4 |
| Basic component | 4.0 | 3.9 | 5.0 | 4.4 |
| Main peak content | 99.4 | 99.4 | 99.3 | 99.2 |

Values are %.

Freeze-Thaw Stability Testing of Antibody 1

Antibody 1 at 10 mg/mL is tested for freeze-thaw stability in the formulation F6. Antibody 1 in the aforementioned formulation in Example 5 is aseptically dispensed in to glass vials, and is sealed with rubber stoppers and plastic covers and is incubated at −80° C. followed by a thaw cycle at room temperature. The freeze-thaw cycle is repeated up to 6 times for the same sample. The samples are tested for stability prior to freezing, and at the $3^{rd}$ and $6^{th}$ thaw cycles, using CEX-HPLC and SEC-HPLC technology.

The freeze-thaw stability test results are illustrated in Table 9. The results demonstrate that the purity and the overall stability of Antibody 1 in the aforementioned formulation was not significantly affected after 6 cycles. Further analysis on appearance, concentration, turbidity also showed similar results. The formulation was thus shown to be able to maintain the stability of Antibody 1 for 6 freeze-thaw cycles.

TABLE 9

CEX-HPLC and SEC-HPLC results of freeze-thaw stability testing at −80° C. on Antibody 1

| | 0 times | 3 times | 6 times |
|---|---|---|---|
| Acidic component | 17.6 | 17.8 | 17.7 |
| Main component | 78.7 | 78.3 | 78.5 |
| Basic component | 3.7 | 3.9 | 3.8 |
| Main peak content | 98.7 | 98.5 | 98.5 |

Values are %.

As demonstrated in the aforementioned examples, extensive testing was performed in order to develop a formulation which is able to maintain the stability of a recombinant human anti-programmed cell death-1 (PD-1) monoclonal antibody under varying conditions. A new and unique formulation, with an unexpected combination of ingredients that provide properties which can improve the physical and chemical stability of the anti-PD-1 antibody, by providing anti-oxidative properties, extending shelf life, and potentially enhancing the clinical safety of the antibody. A unique formulation which enables the anti-PD-1 antibody to maintain chemical and physical stability under strenuous conditions, and varying temperatures ranging from 2-8° C., 25° C., 37° C. and −80° C.

```
Sequences
(human PD-1)
                                              SEQ ID NO: 1
MQIPQAPWPVVWAVLQLGWRPGWFLDSPDRPWNPPTFSPALLVVTEG

DNATFTCSFSNTSESFVLNWYRMSPSNQTDKLAAFPEDRSQPGQDCR

FRVTQLPNGRDFHMSVVRARRNDSGTYLCGAISLAPKAQIKESLRAE

LRVTERRAEVPTAHPSPSPRPAGQFQTLVVGVVGGLLGSLVLLVWVL

AVICSRAARGTIGARRTGQPLKEDPSAVPVFSVDYGELDFQWREKTP

EPPVPCVPEQTEYATIVFPSGMGTSSPARRGSADGPRSAQPLRPEDG

HCSWPL (Light chain)
                                              SEQ ID NO: 2
DIQMTQSPSSVSASVGDRVTITCRASQGISSWLAWYQQKPGKAPKLL

ISAASSLQSGVPSRFSGSGSGTDFTLTISSLQPEDFATYYCQQANHL

PFTFGGGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC (Heavy chain)
                                              SEQ ID NO: 3
QVQLVQSGAEVKKPGSSVKVSCKASGGTFSSYAISWVRQAPGQGLEW

MGLIIPMFDTAGYAQKFQGRVAITVDESTSTAYMELSSLRSEDTAVY

YCARAEHSSTGTFDYWGQGTLVTVSSASTKGPSVFPLAPCSRSTSES

TAALGCLVKDYFPEPVTVSWNSGALTSGVHTFPAVLQSSGLYSLSSV

VTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLP

SSIEKTISKAKGQPREPQVYTLPPSQEEMTKNQVSLTCLVKGFYPSD

IAVEWESNGQPENNYKTTPPVLDSDGSFFLYSRLTVDKSRWQEGNVF

SCSVMHEALHNHYTQKSLSLSLGK (Heavy chain)
                                              SEQ ID NO: 4
QVQLVQSGAEVKKPGSSVKVSCKASGGTFSSYAISWVRQAPGQGLEW

MGLIIPMFDTAGYAQKFQGRVAITVDESTSTAYMELSSLRSEDTAVY

YCARAEHSSTGTFDYWGQGTLVTVSSASTKGPSVFPLAPCSRSTSES

TAALGCLVKDYFPEPVTVSWNSGALTSGVHTFPAVLQSSGLYSLSSV

VTVPSSSLGTKTYTCNVDHKPSNTKVDKRVESKYGPPCPPCPAPEAA

GGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLP

SSIEKTISKAKGQPREPQVYTLPPSQEEMTKNQVSLTCLVKGFYPSD

IAVEWESNGQPENNYKTTPPVLDSDGSFFLYSRLTVDKSRWQEGNVF

SCSVMHEALHNHYTQKSLSLSLG
```

We claim:

1. A pharmaceutical formulation comprising:
   an anti-PD-1 antibody at a concentration of about 5 mg/mL to about 15 mg/mL;
   citrate at a concentration of about of about 15 mM to about 25 mM;
   histidine at a concentration of about 20 mM to about 30 mM;
   mannitol at a concentration of about 130 mM to about 165 mM;
   sodium chloride at a concentration of about 45 mM to about 55 mM;
   edetate at a concentration of about 0.01 mM to about 0.03 mM; and
   polysorbate 20 or polysorbate 80 at a concentration of about 0.01% to about 0.03%;
   and having pH from about 5.5 to about 6.5;
   wherein the anti-PD-1 antibody comprises two light chains (LCs) and two heavy chains (HCs), wherein the amino acid sequence of both LCs is SEQ ID NO: 2 and the amino acid sequence of both HCs is the same and is either SEQ ID NO: 3 or SEQ ID NO: 4.

2. The formulation of claim 1, wherein the amino acid sequence of both HCs is SEQ ID NO: 3.

3. The formulation of claim 1, wherein the amino acid sequence of both HCs is SEQ ID NO: 4.

4. The formulation of claim 1, wherein the concentration of anti-PD-1 antibody is about 10 mg/mL.

5. The formulation of claim 1, wherein the concentration of polysorbate-80 is about 0.02%.

6. The formulation of claim 1, wherein the concentration of polysorbate-20 is about 0.02%.

7. The formulation of claim 1, wherein the concentration of citrate is 20 mM.

8. The formulation of claim 1, wherein the concentration of histidine is 25 mM.

9. The formulation of claim 1, wherein the concentration of mannitol is 140 mM.

10. The formulation of claim 1, wherein the concentration of sodium chloride is 50 mM.

11. The formulation of claim 1, wherein the pH is 6.0.

12. The pharmaceutical formulation of claim 1 in which the concentration of the anti-PD-1 antibody is about 10 mg/mL, the concentration of citrate is about 20 mM, the concentration of histidine is about 25 mM, the concentration of mannitol is about 140 mM, the concentration of sodium chloride is about 50 mM, the concentration of edetate is about 0.02 mM, the concentration of polysorbate-80 is about 0.02%, and the pH is about 6.0.

13. A method of treating cancer comprising administering to a patient in need thereof an effective amount of a pharmaceutical formulation of claim 1.

14. A pharmaceutical formulation of claim 1 for use in cancer.

* * * * *